(12) United States Patent
Toome

(10) Patent No.: US 12,741,129 B2
(45) Date of Patent: Sep. 22, 2026

(54) MEDICAL DEVICE AND METHOD OF USING THE SAME

(71) Applicant: Birgit Toome, Atlantic City, NJ (US)

(72) Inventor: Birgit Toome, Atlantic City, NJ (US)

( * ) Notice: Subject to any disclaimer, the term of this patent is extended or adjusted under 35 U.S.C. 154(b) by 0 days.

(21) Appl. No.: 19/037,159

(22) Filed: Jan. 25, 2025

(65) Prior Publication Data

US 2026/0216488 A1 Jul. 30, 2026

(51) Int. Cl.

| | |
|---|---|
| ***A61M 37/00*** | (2006.01) |
| ***A61M 5/20*** | (2006.01) |
| ***A61M 5/315*** | (2006.01) |
| ***A61M 5/32*** | (2006.01) |
| ***A61M 5/50*** | (2006.01) |

(52) U.S. Cl.

CPC ...... *A61M 37/0015* (2013.01); *A61M 5/2033* (2013.01); *A61M 5/3157* (2013.01); *A61M 5/3298* (2013.01); *A61M 5/5086* (2013.01); *A61M 2037/0023* (2013.01); *A61M 2037/0061* (2013.01); *A61M 2205/6018* (2013.01)

(58) Field of Classification Search

CPC ...... A61M 37/0015; A61M 2037/0023; A61M 2037/0061; A61M 5/20; A61M 2037/0046; A61M 5/3298; A61M 5/2033; A61M 5/3157; A61M 5/5086; A61M 2205/6018; A61M 2037/003; A61M 2037/0038; A61M 2037/0053; A61K 9/0021

See application file for complete search history.

(56) References Cited

U.S. PATENT DOCUMENTS

| | | | | |
|---|---|---|---|---|
| 3,467,096 A * | 9/1969 | Horn | ........................ | A61M 5/46 604/173 |
| 3,572,336 A * | 3/1971 | Hershberg | .......... | A61M 5/2066 604/173 |
| 3,595,231 A | 7/1971 | Pistor | | |

(Continued)

FOREIGN PATENT DOCUMENTS

| | | | | |
|---|---|---|---|---|
| EP | 0917882 A1 * | 5/1999 | .............. | A61M 5/24 |
| EP | 1086718 A1 * | 3/2001 | ........... | A61B 17/205 |

(Continued)

OTHER PUBLICATIONS

EP 1426662, English Language Machine translation (Year: 2004).*

(Continued)

*Primary Examiner* — Wesley G Harris

(74) *Attorney, Agent, or Firm* — Kattina V Barsik, Esq.

(57) ABSTRACT

Disclosed is a medical device including a base body with a release injectable button and a spring-loaded plunger mechanism. The medical device includes the release injectable button coupled to the base body and configured to activate the spring-loaded plunger mechanism. A detachable needle cartridge is removably coupled to the base body and includes a liquid chamber and a plurality of needles. A wand is removably coupled to the base body and includes a detach insert button configured to unlock a locking mechanism coupling the wand to the base body. After the needle cartridge is detached, the wand can be removed and autoclaved. The detachable needle cartridge further includes a filling channel on its outer surface to facilitate filling of the liquid chamber. The device may also include a one-way valve coupled to the plurality of needles.

24 Claims, 8 Drawing Sheets

(56) References Cited

U.S. PATENT DOCUMENTS

| | | | | |
|---|---|---|---|---|
| 4,693,708 | A * | 9/1987 | Wanderer | A61M 5/3271 604/263 |
| 10,433,928 | B2 | 10/2019 | Unger | |
| 2007/0021717 | A1* | 1/2007 | Gabel | A61M 37/0015 604/93.01 |
| 2007/0038181 | A1* | 2/2007 | Melamud | A61B 17/3478 606/186 |

FOREIGN PATENT DOCUMENTS

| | | | | |
|---|---|---|---|---|
| EP | 1426662 | A1 * | 6/2004 | F04B 3/164 |
| JP | 2005087521 | A * | 4/2005 | A61M 5/3298 |
| KR | 20100064669 | A * | 6/2010 | A61M 5/158 |
| WO | WO-0202180 | A2 * | 1/2002 | A61B 10/0045 |
| WO | WO-2004000389 | A2 * | 12/2003 | A61K 9/0021 |
| WO | WO-2009023798 | A2 * | 2/2009 | A61M 5/3287 |
| WO | WO-2016006409 | A1 * | 1/2016 | A61M 5/3298 |
| WO | WO-2017189259 | A2 * | 11/2017 | A61M 37/0015 |

OTHER PUBLICATIONS

JP 2005087521, English Language Machine Translation (Year: 2005).*
KR 20100064669, English Language Machine Translation (Year: 2010).*
WO 2016006409, English Language Machine Translation (Year: 2016).*
EP-0917882-A1, English language machine translation (Year: 1999).*

* cited by examiner

MEDICAL DEVICE AND METHOD OF USING THE SAME

TECHNICAL FIELD

The present disclosure relates to a medical device, more particularly the present disclosure relates to a multi-needle injection device, a detachable needle cartridge, and a method of using thereof.

BACKGROUND

A needle injection system has been known and used for many years for various medical purposes. The needle injection system is frequently used in clinical medicine to administer injections, infuse intravenous therapy into the bloodstream, apply compounds such as glue or lubricant, and draw/measure liquids. Various types of needle injection systems have been developed with time to address issues such as pain reduction, speed of drug delivery, and precision in various treatments. On the other hand, the evolution of injection system has been improved based on the design of needles, improvements in materials and manufacturing processes of the needle injection system.

The introduction of the disposable syringes has revolutionized the medical field. The disposable needle injection system helped in reducing the risk of injections and make medicinal procedures more hygienic.

However, the present needle injection systems include only single needle configurations for administering medicine into the blood vessel or skin of a subject. The single needle systems are often time-consuming and painful, which is problematic in critical situations, leading to increased pain for subjects and procedure length. Micro-needles, which are commonly used for transdermal drug delivery and cosmetic treatments, prep the skin for medication topically. Micro-needles put holes in the skin as needles rub on the skin, they are very small holes in the skin, it is not the same as the present invention which actually delivers products or medicines into the skin by injection. The multi-needle systems, primarily used in microneedles for transdermal drug delivery and cosmetic treatments, are limited in their application scope. These systems are inefficient for reuse, have rough ejection mechanisms, and lack safety features for secure shipping, storage, and prevention of accidental use. Furthermore, they struggle to accurately administer to a larger area of the skin. Although advanced automatic and needle-less injection systems exist, they pose significant concerns regarding proper disposal and ease of use, and efficient drug delivery of cosmetic products like exosome delivered growth factor for hair growth and other substances like botox and hyaluronic acid plumping products.

The present injection methods deliver products via multiple injections of single needles which may cause post treatment redness, swelling and increased pain to a patient not to mention increased treatment time. Therefore there is a need for an advanced injection system for targeted and precise delivery of exosomes and other substances mentioned above, to specific tissues, optimizing therapeutic outcomes.

Therefore, there is a need for a technical solution that addresses these issues in the present needle injection systems, particularly those with multiple needles.

SUMMARY

In an aspect of the present disclosure, a method for injecting medicine through a medical device is disclosed. The method includes a step of filling a medicine inside one or more liquid chambers integrated inside a detachable needle cartridge by way of a filling channel. Furthermore, the method includes a step of attaching the detachable needle cartridge to a base body by way of a connection means. Furthermore, the method includes a step of injecting the medicine through a plurality of needles of the detachable needle cartridge into a subject upon manually pushing a release injectable button by way of a spring-loaded plunger mechanism associated with the base body. Furthermore, the method includes a step of detaching a wand of the medical device from the base body upon manually pushing a detach insert button by way of a locking mechanism associated with the base body.

In some embodiments of the present disclosure, the filing channel of the detachable needle cartridge further includes a tamper-evident seal, and a closure cap disposed on the tamper-evident seal.

In some embodiments of the present disclosure, the filing channel has a plastic material selected from a group of polypropylene, polycarbonate, polyethylene, polystyrene, or silicone.

In another aspect of the present disclosure, a medical device is disclosed. The medical device includes a base body, a detachable needle cartridge and a wand. The base body includes a release injectable button and a spring-loaded plunger mechanism. Further, the medical device includes the detachable needle cartridge coupled to the base body. The detachable needle cartridge includes one or more liquid chambers integrated inside the detachable needle cartridge and configured to hold the liquid. The detachable needle cartridge includes a filling channel disposed on an outer surface of the detachable needle cartridge and facilitates filing of the liquid in one or more liquid chambers. The detachable needle cartridge includes a plurality of needles coupled to one or more liquid chambers. Furthermore, the medical device includes the wand coupled to the base body. The wand includes a detach insert button. The base body is adapted to activate the spring-loaded plunger mechanism by manually pushing the release injectable button and releases the liquid into the plurality of needles of the detachable needle cartridge to be injected into a subject. The wand is adapted to attach and detach from the base body by way of a locking mechanism activated by manually pushing the detach insert button.

In some embodiments of the present disclosure, the spring-loaded plunger mechanism further includes a spring adapted to maintain an expanded state before injecting the liquid into the detachable needle cartridge and attains a compressed state upon activation of the release injectable button to inject the liquid into the detachable needle cartridge.

In some embodiments of the present disclosure, the wand further includes the locking mechanism selected from a group of looking teeth, latch bolt, locking pin, or bayonet fitting.

In some embodiments of the present disclosure, the base body is at least one of a paddle-shape.

In some embodiments of the present disclosure, the release injectable button and detach insert button further include tactile or audible feedback to indicate the pushing of each button.

In some embodiments of the present disclosure, the base body includes a metal material selected from a group of stainless steel, titanium, or coated aluminum.

In some embodiments of the present disclosure, the detachable needle cartridge has a disposable and heat-resistant material selected from a group of polypropylene, polycarbonate, polyethylene, polystyrene, or silicone.

In some embodiments of the present disclosure, the liquid is at least one of a medicine, drug, antibiotics, pharmaceutical compositions, cosmetic liquids or gels.

In some embodiments of the present disclosure, the detachable needle cartridge further includes a connection means selected from a group of sliding fits, snap-fit, push-fit, bayonet fitting, or threaded-fitting.

In some embodiments of the present disclosure, the one or more liquid chambers have a volume in the range between 1.5 to 8 cubic centimeters.

In some embodiments of the present disclosure, the needles have a material selected from a group of stainless steel, nickel-plated steel, or alloy coated aluminum needles.

In some embodiments of the present disclosure, the plurality of needles of the detachable needle cartridge are inclined at an acute angle to facilitate insertion of the needles into the subject with ease.

In an aspect of the present disclosure, a detachable needle cartridge is disclosed. The detachable needle cartridge includes one or more liquid chambers, a filling channel, a plurality of needles, a one-way-valve and a connection means. The detachable needle cartridge includes one or more liquid chambers integrated inside the detachable needle cartridge and configured to hold liquid. The detachable needle cartridge includes the filling channel disposed on an outer surface of the detachable needle cartridge and facilitates filing of the liquid in the liquid chambers. The detachable needle cartridge includes the plurality of needles coupled to the one or more liquid chambers. The detachable needle cartridge includes the one-way valve integrated with the plurality of needles. The detachable needle cartridge includes the connection means. The detachable needle cartridge is coupled to a base body by way of the connection means and is adapted to deliver the liquid through plurality of needles into a subject.

In some embodiments of the present disclosure, the detachable needle cartridge further includes a spring-loaded autoinjector instead of the plurality of needles.

In some embodiments of the present disclosure, the spring-loaded autoinjectors is retracted back after the complete injection of medicine from the one or more liquid chambers to prevent tissue damage and minimize pain discomfort.

In some embodiments of the present disclosure, the detachable needle cartridge further includes the connection means selected from a group of sliding fit, snap-fit, push-fit, bayonet fitting, or threaded-fitting.

In some embodiments of the present disclosure, the plurality of needles includes 20, 30, or 40 needles depending on the treatment procedure.

In some embodiments of the present disclosure, the detachable needle cartridge further includes a needle shield coupled with the plurality of needles of the detachable needle cartridge.

In some embodiments of the present disclosure, the plurality of needles of the detachable needle cartridge are inclined at an acute angle to facilitate easy insertion of the plurality of needles into the subject.

In some embodiments of the present disclosure, the detachable needle cartridge further includes an indicator or marking on the detachable needle cartridge that ensures proper fitting of the detachable needle cartridge in the base body.

In some embodiments of the present disclosure, the plurality of needles has a material selected from a group of stainless steel, nickel-plated steel, or alloy coated aluminum needles.

In some embodiments of the present disclosure, the needle cartridge has a disposable a disposable and heat-resistant material selected from a group of polypropylene, polycarbonate, polyethylene, polystyrene, or silicone.

BRIEF DESCRIPTION OF THE DRAWINGS

The following detailed description of the preferred embodiments of the present disclosure will be better understood when read in conjunction with the appended drawings. The present disclosure is illustrated by way of example, and not limited by the accompanying figures, in which references indicate similar elements.

DETAILED DESCRIPTION

The detailed description of the appended drawings is intended as a description of the currently preferred embodiments of the present disclosure and is not intended to represent the only form in which the present disclosure may be practiced. It is to be understood that the same or equivalent functions may be accomplished by different embodiments that are intended to be encompassed within the spirit and scope of the present disclosure.

Figure 1:
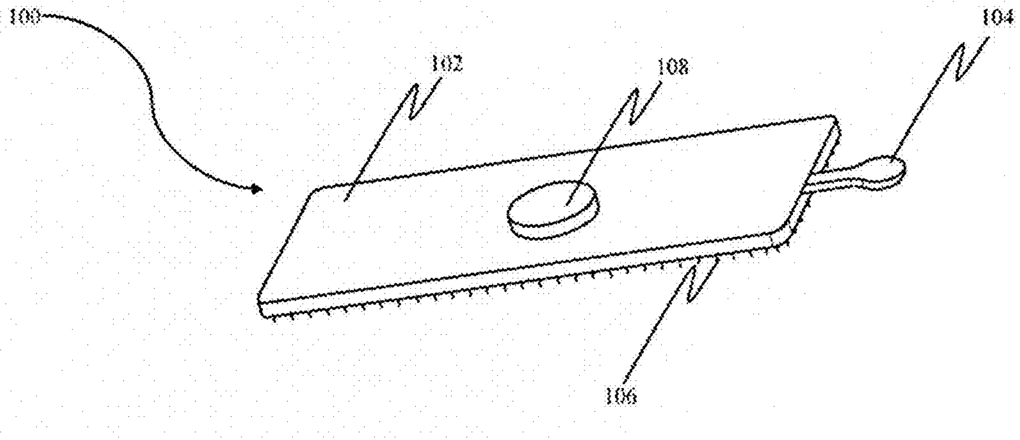
FIG. 1 illustrates a perspective view of a medical device, respectively, according to an embodiment of the present disclosure.

FIG. 1 illustrates a perspective view of a medical device, respectively, according to an embodiment of the present disclosure. The present disclosure relates to a medical device 100 designed to facilitate controlled delivery of medicine into a subject. The medical device 100 may include a base body 102, which may house a spring-loaded plunger mechanism (shown later in FIG. 4A) and a release injectable button 108. The base body 102 may be adapted with the release injectable button 108, which when pushed, may activate the spring-loaded plunger mechanism to release medicine into a plurality of needles (shown later in FIG. 3A-3C) of a detachable needle cartridge 106.

The detachable needle cartridge 106, which may be removably coupled to the base body 102 and may include the plurality of needles and a filling channel (shown later in FIG. 4A) disposed on its outer surface to facilitate the filling of a liquid chamber (shown later in FIG. 4A). In some aspects, the detachable needle cartridge 106 may also include a one-way valve (shown later in FIG. 5) coupled to the plurality of needles.

In another embodiment of the present disclosure, the needles may be inclined at an acute angle to facilitate easy insertion into the subject.

The medical device 100 may also include a wand 104 that may be removably coupled to the base body 102. The wand 104 may include a detach insert button (shown later in FIG. 2A-2C) that may be adapted to unlock a locking mechanism (shown later in FIG. 4A) which facilitates coupling of the wand 104 to the base body 102. The locking mechanism may allow for easy detachment of the wand 104 from the base body 102, facilitating cleaning, sterilizing or autoclaving of the base body 102 after the injection process.

In another embodiment of the present disclosure, the medical device 100 may include tactile or audible feedback after complete injection of the liquid, offering an additional layer of subject assurance. The medical device 100 may be adapted to accommodate a variety of medicines, drugs, antibiotics, pharmaceutical compositions, cosmetic liquids or gels and the like, providing a versatile solution for various medical applications.

The release injectable button 108 of the injection device medical device 100, when pushed, may activate the spring-loaded plunger mechanism, initiating the injection process. The release injectable button 108 may be designed to be easily accessible and comfortable to use, considering factors such as grip and tactile feedback. In some embodiment of the present disclosure, the release injectable button 108 may be circular or oval-shaped, but other shapes may also be used depending on the specific design of the medical device 100.

Figures 2A, 2B, 2C:
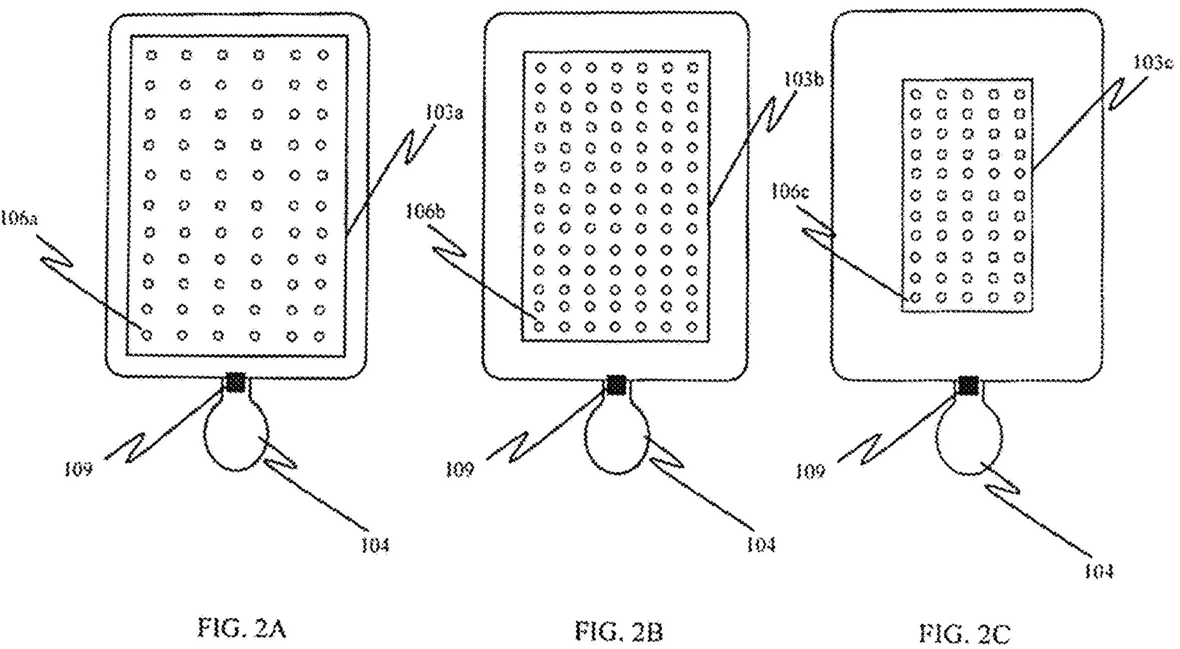
FIG. 2A-2C illustrates a front view of the medical device coupled with multiple types of detachable needle cartridge, according to an embodiment of the present disclosure.

FIG. 2A-2C illustrates a front view of the medical device coupled with multiple types of detachable needle cartridge, according to an embodiment of the present disclosure. The detachable needle cartridge 106 of the medical device 100 may include multiple types of detachable needle cartridges (106*a*, 106*b*, 106*c*) coupled to the base body 102 by way of a connection means (103*a*, 103*b*, 103*c*). In some embodiment of the present disclosure, the coupling mechanism may be facilitated by the connection means (103*a*, 103*b*, 103*c*), which may be selected from a group of sliding fit, snap-fit, push-fit, bayonet fitting, threaded-fitting, and the like. The coupling mechanism allows for easy attachment and detachment of the detachable needle cartridge 106, facilitating replacement or cleaning of the detachable needle cartridge 106.

The medical device 100 may further include the wand 104 coupled to the base body 102 by way of the locking mechanism. The wand 104 may include the detach insert button 109, which may be adapted to unlock the locking mechanism coupling the wand 104 to the base body 102. In another aspect of the present disclosure, upon pressing the detach insert button 109, the wand 104 may be detached from the base body 102, allowing for easy removal of the detachable needle cartridge 106.

In some aspects of the present disclosure, the detach insert button 109 may operate through the locking mechanism. This mechanism may allow for easy attachment and detachment of the wand 104 from the base body 102. The locking mechanism of the wand 104, but not limited to, may be selected from a group of locking teeth, latch bolt, locking pin, bayonet, and the like, providing flexibility in design and operation.

Figures 3A, 3B, 3C:
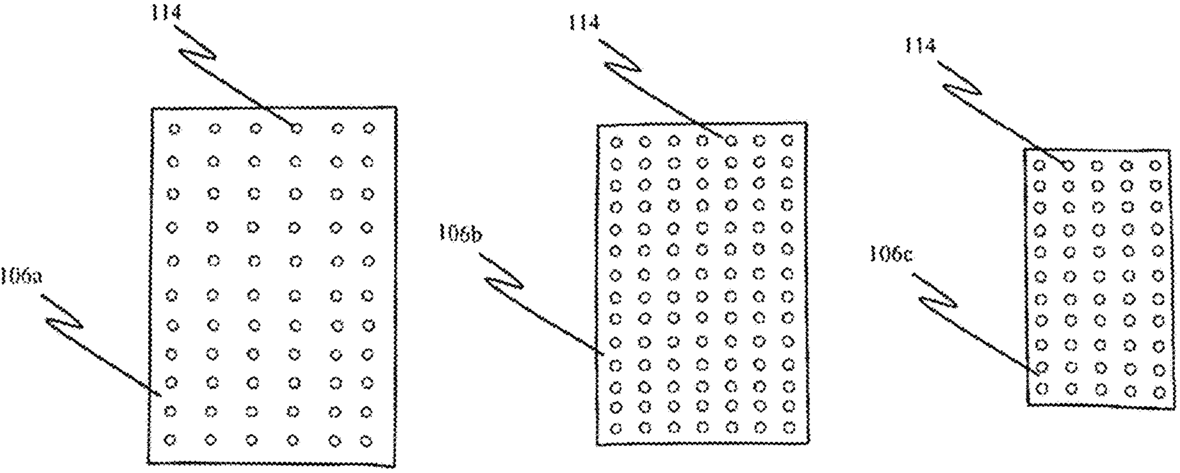
FIG. 3A-3C illustrates a front view of the multiple types of detachable needle cartridges of FIG. 2A-2C, according to an embodiment of the present disclosure.

FIG. 3A-3C illustrates a front view of the multiple types of detachable needle cartridges of FIG. 2A-2C, according to an embodiment of the present disclosure. The detachable needle cartridge 106 of the medical device 100 may include multiple types of detachable needle cartridges (106*a*, 106*b*, 106*c*) coupled to the base body 102 by way of the connection means (103*a*, 103*b*, 103*c*). The detachable needle cartridge 106 further may include the plurality of needles 114, which may be used to inject the liquid into the subject.

In some aspects of the present disclosure, the plurality of needles 114 may be 20, 30, or 40, or any other suitable number depending on the specific treatment procedure. In another embodiment, the plurality of needles 114 within the cartridge 106 may be made from materials, but not limited to, such as stainless steel, nickel-plated steel, or alloy coated aluminum needles.

Figure 4A:
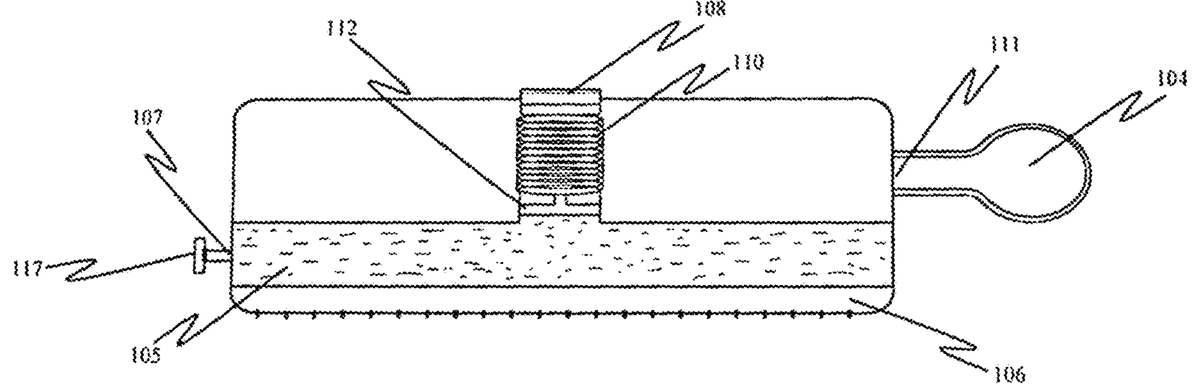
FIGS. 4A & 4B illustrates a side view of the medical device with spring-loaded plunger mechanism in expanded and compressed state respectively, according to an embodiment of the present disclosure.
Figure 4B:
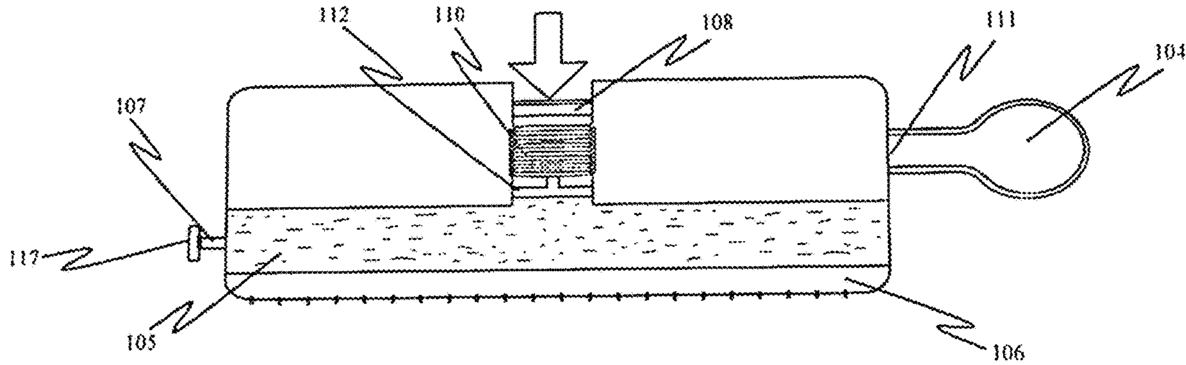

FIGS. 4A & 4B illustrates a side view of the medical device with spring-loaded plunger mechanism in expanded and compressed state respectively, according to an embodiment of the present disclosure. The spring-loaded plunger mechanism, which may be activated by pushing the release injectable button 108, may include several components. The components may include a spring 110, a plunger 112, and a one-way valve 116. The spring 110 may be in an expanded state before the injection process begins. Upon pushing the release injectable button 108, the spring 110 may compress, pushing the plunger 112 forward. The forward movement of the plunger 112 may compress the liquid in the liquid chamber 105, forcing it through the plurality of needles 114 of the detachable needle cartridge 106 and into the subject.

In some embodiments of the present disclosure, the spring-loaded plunger mechanism may be designed to return to its original position after the injection process. This may be facilitated by the spring 110 returning to its expanded state after the release injectable button is released 108. This feature may allow the medical device 100 to be ready for subsequent use without the need for manual resetting of the mechanism.

In another embodiment of the present disclosure, the release injectable button 108 and the spring-loaded plunger mechanism may be designed to provide tactile or audible feedback to the subject. The feedback may occur after the complete injection of the medicine, providing an additional layer of subject assurance. The feedback may be generated by the movement of the spring 110 and plunger 112, or it may be generated by a separate feedback mechanism integrated into the medical device 100.

In another embodiment of the present disclosure, the medical device 100 may include safety features to prevent accidental activation of the release injectable button 108 and the spring-loaded plunger mechanism. For instance, a child-resistant mechanism may be incorporated into the design of the release injectable button 108 that require a specific sequence of actions or a certain level of force to activate the button, preventing accidental activation by children or during transportation or storage.

In another embodiment of the present disclosure, the release injectable button 108 and the spring-loaded plunger mechanism may be designed to control the rate of medicine delivery. This may be achieved by adjusting the tension of the spring 110 and the diameter of the plunger 112. By controlling the rate of medicine delivery, the medical device 100 may provide a more comfortable, faster and less painful injection experience for the subject.

In some other embodiments of the present disclosure, the release injectable button 108 and the spring-loaded plunger mechanism may be designed to ensure accurate and complete delivery of the medicine. This may be facilitated by the design of the liquid chamber 105 and the one-way valve 116.

The one-way valve 116 may prevent backflow of the medicine, ensuring that the entire volume of medicine is delivered to the subject. The liquid chamber 105 may be designed to ensure efficient and complete expulsion of the liquid or medicine during the injection process.

In some aspects of the present disclosure, the release injectable button 108 and the spring-loaded plunger mechanism may be integrated into a single unit. In another aspect of the present disclosure, these components may be separate, allowing for easier replacement or maintenance of individual components. Regardless of the specific design, the release injectable button 108 and the spring-loaded plunger mechanism may be designed to work together to provide a reliable and efficient injection process.

Figure 5:
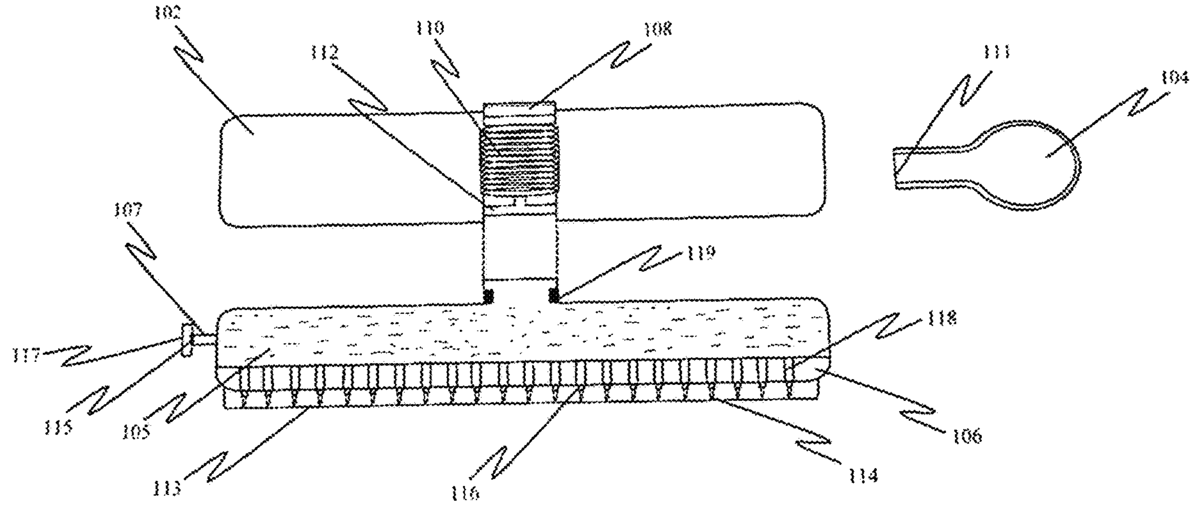
FIG. 5 illustrates an exploded view of the medical device, according to an embodiment of the present disclosure.

FIG. 5 illustrates an exploded view of the medical device, according to an embodiment of the present disclosure. The detachable needle cartridge 106 of the medical device 100. The detachable needle cartridge 106 may be designed to hold the liquid to be injected and may be removably coupled to the base body 102. The base body 102 can be sterilized in an autoclave. The detachable needle cartridge 106 is disposable. The coupling mechanism may be facilitated by a connection means (103*a*, 103*b*, 103*c*), which may be selected from a group of sliding fit, snap-fit, push-fit, bayonet fitting, threaded-fitting, and the like. This allows for easy attachment and detachment of the detachable needle cartridge 106, facilitating replacement or cleaning of the detachable needle cartridge 106.

The detachable needle cartridge 106 further may include the plurality of needles 114, which may be used to inject the liquid into the subject. In another embodiment of the present disclosure, the needles 114 may be inclined at an acute angle to facilitate easy insertion into the subject. This design may reduce the discomfort experienced by the subject during the injection process. In some aspects of the present disclosure, the plurality of needles 114 may be 20, 30, or 40, or any other suitable number depending on the specific treatment procedure.

In some aspects of the present disclosure, the plurality of syringe barrels 118 may be integrated inside the detachable needle cartridge 106 such that medicine from the liquid chamber 105 is distributed in equal amount to the plurality of syringe barrels 118. The medicine from the plurality of syringe barrel 118 may be injected into the subject through plurality of needles 114 of the detachable needle cartridge 106.

In some aspects of the present disclosure, the detachable needle cartridge 106 may include one or more liquid chambers 105 adapted to hold the liquid. The liquid chamber 105 may be designed to hold a specific volume of liquid, which may range between 1.5 to 8 cubic centimeters, or any other suitable volume depending on the specific application. The liquid chamber 105 may be designed to ensure efficient and complete liquid or medicine expulsion during the injection process.

The detachable needle cartridge 106 may also include the filling channel 107 on its outer surface, which may facilitate the filling of the liquid chamber 105. The filling channel 107 may be designed to allow for easy and efficient filling of the liquid chamber 105, reducing the time and effort required for the filling process. The filling channel 107 may be made of a plastic material selected from the group of polypropylene, polycarbonate, polyethylene, polystyrene, silicone, or any other suitable material known in the art.

In some aspects of the present disclosure, the detachable needle cartridge 106 may be made of a disposable and heat-resistant materials selected from the group of polypropylene, polycarbonate, polyethylene, polystyrene, or silicone. These materials may offer flexibility, heat resistant and ease of disposal after use. The base body 102 can be sterilized in an autoclave and reused. The detachable needle cartridge 106 is disposable. The In another aspect, the detachable needle cartridge 106 may be made from other suitable materials known in the art.

In some aspects of the present disclosure, the detachable needle cartridge 106 may include the one-way valve 116 coupled to the plurality of needles 114. The one-way valve 116 may allow the liquid or medicine to flow in one direction only, preventing backflow and ensuring efficient delivery of the medicine or liquid. In another embodiment of the present disclosure, the detachable needle cartridge 106 may also include a sensor (not shown), such as a pressure sensor, a flow rate sensor, or an optical sensor, to detect liquid depletion in the liquid chamber 105. The sensor may provide an additional layer of assurance to the subject, indicating when the liquid chamber 105 is empty and needs to be refilled.

In another embodiment of the present disclosure, the detachable needle cartridge 106 may be designed to provide tactile or audible feedback after the complete injection of the liquid. The feedback may serve to indicate to the subject that the injection process has been successfully completed, enhancing the subject experience and ensuring proper operation of the medical device 100.

As used herein, "detachable needle cartridge 106" refers to the component of the medical device 100 that houses the plurality of needles 114 and the liquid inside the liquid chamber 105 to be injected. The detachable needle cartridge 106 may be designed to be easily attached and detached from the base body 102, facilitating replacement or cleaning of the detachable needle cartridge 106.

The wand 104 that may be coupled to the base body 102, may serve various functions in the operation of the medical device 100. In some aspects of the present disclosure, the wand 104 may be designed to facilitate the attachment and detachment from the base body 102. This may be particularly useful for cleaning, sterilizing or autoclaving the base body 102 after the injection process. The wand 104 may include the detach insert button 109, which may be adapted to unlock a locking mechanism 111 coupling the wand 104 to the base body 102. In another aspect of the present disclosure, upon pushing the detach insert button 109, the wand 104 may be detached from the base body 102, allowing for easy removal of the detachable needle cartridge 106.

In some aspects of the present disclosure, the detach insert button 109 may operate through the locking mechanism 111. The locking mechanism 111 may allow for easy attachment and detachment of the wand 104 from the base body 102. The locking mechanism 111 of the wand 104 may be selected from the group of locking teeth, latch bolt, locking pin, bayonet, and the like, providing flexibility in design and operation.

In another embodiment of the present disclosure, the detach insert button 109 may provide tactile or audible feedback after pressing. The feedback may serve to indicate to the subject that the button has been successfully pressed and the wand 104 has been detached from the base body 102, enhancing the subject experience and ensuring proper operation of the medical device 100.

In another embodiment of the present disclosure, the wand 104 may be designed to be easily gripped and manipulated by the subject. The wand 104 may be ergonomically designed to fit comfortably in the subject's hand, facilitating easy operation of the detach insert button 109 and the overall use of the medical device 100. The wand 104 may be made of a variety of materials, including but not limited to plastic, metal, or a combination thereof. In another embodiment of the present disclosure, the wand 104 may be designed to be reusable, allowing for repeated use with multiple detachable needle cartridges (106*a*, 106*b*, 106*c*). In other cases, the wand 104 may be designed to be disposable, facilitating easy disposal after use. Regardless of the specific design, the wand 104 may be designed to work in conjunction with the base body 102, the release injectable button 108, and the detachable needle cartridge 106 to provide a reliable and efficient injection process.

As used herein, "wand 104" refers to the component of the medical device 100 that facilitates the attachment and detachment from the base body 102. The wand 104 may include a detach insert button 109, which may be adapted to unlock the locking mechanism 111 coupling the wand 104 to the base body 102.

In another embodiment of the present disclosure, the locking mechanism 111 of the wand 104 may include a variety of locking options. In some aspects of the present disclosure, the locking mechanism 111 may include locking teeth that engage with corresponding grooves or notches on the base body 102. In another aspect of the present disclosure, the locking mechanism 111 may include a latch bolt, a locking pin, a bayonet, or any other suitable locking device known in the art. The locking mechanism 111 may provide flexibility in design and operation, allowing for easy attachment and detachment of the wand 104 from the base body 102.

In some aspects of the present disclosure, the locking mechanism 111 may be designed to provide a secure and reliable connection between the wand 104 and the base body 102. This may ensure that the wand 104 remains firmly attached to the base body 102 during the injection process, preventing accidental detachment and ensuring proper operation of the device. The locking mechanism 111 may also be designed to be easily activated by the detach insert button 109, facilitating easy detachment of the wand 104 from the base body 102 after the injection process.

The locking mechanism 111 may be designed to return to its original position after the detach insert button 109 is released. This may allow the wand 104 to be easily reattached to the base body 102, readying the medical device 100 for subsequent use.

As used herein, "spring-loaded plunger mechanism" refers to the component of the medical device 100 that facilitates the injection of the liquid into the detachable needle cartridge 106. The spring-loaded plunger mechanism may be activated by the release injectable button 108 and may include the spring 110 and the plunger 112 that work together to facilitate the injection process.

The detachable needle cartridge 106 may include the filling channel 107 on its outer surface. This filling channel 107 may be designed to facilitate the filling of the liquid into the one or more liquid chambers 105 inside the detachable needle cartridge 106.

In another embodiment of the present disclosure, the filling channel 107 may include a closure cap 117 and a tamper-evident seal 115. The closure cap 117 may be designed to securely seal the filling channel 107 after the liquid has been filled into the liquid chamber 105, preventing leakage or spillage of the liquid. The tamper-evident seal 115 may be designed to provide visible evidence if the filling channel 107 has been tampered with or opened after the liquid has been filled. This feature may serve to ensure the integrity and sterility of the liquid in the liquid chamber 105, preventing contamination by moisture, oxygen, or other contaminants.

In another embodiment of the present disclosure, the filling channel 107 may be designed to accommodate a variety of filling methods. For instance, the filling channel 107 may be designed to accommodate manual filling, where the subject manually pours or injects the liquid or medicine into the liquid chamber 105. Alternatively, the filling channel 107 may be designed to accommodate automated filling, where a machine (not shown) or device (not shown) automatically fills the liquid chamber 105 with the liquid. Regardless of the specific filling method, the filling channel 107 may be designed to ensure efficient and complete filling of the liquid chamber 105, ensuring accurate dosing of the liquid for the injection process.

In another embodiment of the present disclosure, the release injectable button 108 and the detach insert 109 buttons may provide a tactile or audible feedback after pressing. The feedback may serve to indicate to the subject that the button has been successfully pressed, enhancing the subject experience and ensuring proper operation of the device. In another embodiment, the tactile feedback may be provided in the form of a click or a change in resistance felt by the subject when pressing the button. In another embodiment, the audible feedback may be provided in the form of a click or a beep sound heard by the subject when pressing the button. In some aspects of the present disclosure, both tactile and audible feedback may be provided. The feedback mechanism may be integrated into the buttons or maybe a separate component that is activated when the buttons are pressed. The feedback mechanism may be designed to provide a clear and distinct feedback that is easily recognizable by the subject, ensuring that the subject is aware of the successful operation of the buttons. In another embodiment, the feedback mechanism may be designed to provide subtle feedback that is not disruptive or distracting to the subject. Regardless of the specific design, the feedback mechanism may be designed to enhance the subject experience and ensure proper operation of the medical device 100.

In some aspects of the present disclosure, the materials used for the various components of the medical device 100 may vary depending on the specific requirements of the application. For instance, the base body 102 may be composed of metals selected from the group of stainless steel, titanium, or coated aluminum. These materials may offer durability and resistance to corrosion, making them suitable for repeated use. In another aspect, the base body 102 may be made from other suitable materials known in the art.

In some aspects of the present disclosure, the detachable needle cartridge 106 may be made of a disposable and heat-resistant materials selected from the group of polypropylene, polycarbonate, polyethylene, polystyrene, or silicone. These materials may offer flexibility and ease of disposal after use. In another aspect, the detachable needle cartridge 106 may be made from other suitable materials known in the art. In some aspects of the present disclosure, the needles 114 within the cartridge 106 may be made from materials such as stainless steel, nickel-plated steel, or alloy coated aluminum needles. These materials may offer sharpness and durability, ensuring efficient delivery of the medicine into the subject.

In some aspects of the present disclosure, the wand 104 may be made from a variety of materials, including but not limited to plastic, metal, or a combination thereof. The choice of material may depend on factors such as durability, ease of cleaning, and subject comfort. For instance, a metal wand may offer durability and ease of cleaning, while a plastic wand may be lighter and more comfortable to hold.

In some aspects of the present disclosure, the filling channel 107 of the detachable needle cartridge 106 may be made of plastic material selected from the group of polypropylene, polycarbonate, polyethylene, polystyrene, or silicone, or any other suitable material known in the art. This material may offer flexibility and ease of use, facilitating the filling process.

In some aspects of the present disclosure, the release injectable button 108 and the detach insert button 109 may be made from a variety of materials, including but not limited to plastic, metal, or a combination thereof. The choice of material may depend on factors such as durability, ease of use, and subject comfort. For instance, a metal button may offer durability and a solid feel, while a plastic button may be lighter and more comfortable to press.

In some aspects of the present disclosure, the medical device 100 may be designed to accommodate a variety of liquids for injection. These liquids may include, but are not limited to, medicine, drug, antibiotics, pharmaceutical compositions, cosmetic liquids or gels, and the like. The specific type of liquid or medicine used may depend on the specific treatment or medical procedure being performed. For instance, in some aspect, the liquid may be a medicine designed to treat a specific disease or condition. In another aspect, the liquid may be a drug designed to alleviate symptoms or improve the subject condition.

In an aspect of the present disclosure, the medical device 100 may be used for an exosome treatment procedure. The medical device 100 may be designed to inject multiple needles simultaneously that enhances treatment efficiency by covering larger areas with greater precision, reducing the need for extensive treatment times. Furthermore, the medical device 100 may minimize patient downtime while helping to improve several treatment procedures, such as skin rejuvenation, hair restoration, and tissue repair, thereby reducing potential risks.

In another embodiment of the present disclosure, the liquid may be in a variety of forms, including but not limited to, solutions, suspensions, emulsions, or any other suitable form known in the art. The liquid may be stored in the one or more liquid chambers 105 inside the detachable needle cartridge 106, ready for injection into the subject body. The liquid may be filled into the liquid chamber 105 through the filling channel 107 on the outer surface of the detachable needle cartridge 106, facilitating easy and efficient filling of the liquid chamber 105. In some aspect, the liquid may be pre-filled into the liquid chamber 105, allowing for immediate use of the medical device 100. In another aspect, the liquid may be filled into the liquid chamber 105 by the subject or a healthcare professional prior to use. Regardless of the specific type or form of liquid used, the medical device 100 may be designed to ensure efficient and complete delivery of the liquid into the subject body.

In some aspects of the present disclosure, the connection means (103*a*, 103*b*, 103*c*) between the detachable needle cartridge 106 and the base body 102 may be designed to facilitate easy attachment and detachment of the detachable needle cartridge 106. The connection means (103*a*, 103*b*, 103*c*) may be selected from a group of sliding fit, snap-fit, push-fit, bayonet fitting, threaded-fitting, and the like. For instance, in some aspect, a sliding fit connection means may be used, where the detachable needle cartridge 106 slides into place on the base body 102. In another aspect, a snap-fit connection means may be used, where the detachable needle cartridge 106 snaps into place on the base body 102. In another aspect, a push-fit connection means may be used, where the detachable needle cartridge 106 is pushed into place on the base body 102. In preferred aspect, a bayonet fitting may be used, where the detachable needle cartridge 106 is twisted into place on the base body 102. In another aspect, a threaded fitting may be used, where the detachable needle cartridge 106 is screwed into place on the base body 102. Regardless of the specific type of connection means used, the connection means may be designed to provide a secure and reliable connection between the detachable needle cartridge 106 and the base body 102, ensuring proper operation of the injection device medical device 100.

In some aspects of the present disclosure, the injection device medical device 100 may include one or more liquid chambers 105 adapted inside the detachable needle cartridge 106. These liquid chambers 105 may be designed to hold a specific volume of liquid, which may range between 1.5 to 8 cubic centimeters, or any other suitable volume depending on the specific application. The liquid chambers 105 may be designed to ensure efficient and complete expulsion of the liquid during the injection process. The liquid chambers 105 may be in direct communication with the spring-loaded plunger mechanism, facilitating the transfer of liquid from the liquid chamber 105 to the plurality of needles 114 of the detachable needle cartridge 106 upon activation of the release injectable button 108.

In some aspects of the present disclosure, the liquid chamber 105 may interface with other components of the medical device 100. For instance, the liquid chamber 105 may be in direct communication with the filling channel 107, facilitating the filling of the liquid chamber 105 with liquid. The liquid chamber 105 may also interface with the one-way valve 116, ensuring that the medicine flows in one direction only, from the liquid chamber 105 to the detachable needle cartridge 106. In another embodiment, the liquid chamber 105 may also interface with the sensor (not shown), allowing the sensor to detect liquid depletion in the liquid chamber 105. Regardless of the specific design, the liquid chamber 105 may be designed to work in conjunction with other components of the medical device 100 to provide a reliable and efficient injection process.

In another embodiment of the present disclosure, the plurality of needles 114 in the detachable needle cartridge 106 may be inclined at an acute angle. This inclination may facilitate easy insertion of the needles 114 into the subject body. The acute angle may be selected based on factors such as the thickness of the subject skin, the desired depth of injection, and the specific treatment procedure. For instance, a smaller angle may be used for superficial injections, while a larger angle may be used for deeper injections. The inclination of the needles 114 may also help to distribute the medicine more evenly within the subject body, enhancing the effectiveness of the treatment. In preferred aspect of the present disclosure, the needles 114 may be straight, while in other aspects, the needles 114 may be curved or bent to achieve the desired inclination. Regardless of the specific design, the inclined angle of the needles 114 may be designed to provide a comfortable and efficient injection experience for the subject.

Figure 6:
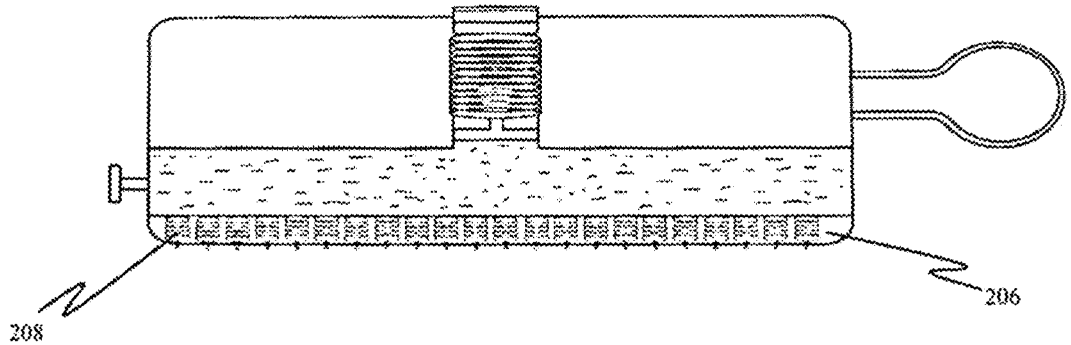
FIG. 6 illustrates another embodiment of the medical device, according to an embodiment of the present disclosure.

FIG. 6 illustrates another embodiment of the medical device, according to an embodiment of the present disclosure. The needles 114 in the detachable needle cartridge 206 may be replaced by autoinjectors 208. The autoinjectors 208 may be designed to automatically inject a pre-filled dose of medicine into the subject body upon activation of the release injectable button 108. The autoinjectors 208 may include a spring-loaded mechanism similar to the spring-loaded plunger mechanism described above, facilitating the injection process. The autoinjectors 208 may be designed to provide a more comfortable and less painful injection experience for the subject, reducing the discomfort associated with traditional needle injections 114. The autoinjectors 208 may be made from materials such as stainless steel, nickel-plated steel, or alloy coated aluminum needles, offering sharpness and durability. In another embodiment, the autoinjectors 208 may be inclined at an acute angle to facilitate easy insertion into the subject body, similar to the needles 114 described above. The number of autoinjectors 208 in the detachable needle cartridge 206 may vary depending on the specific treatment procedure, and may be 20, 30, or 40, or any other suitable number.

The autoinjectors 208 of medical device 100 may include a retraction mechanism for the needles after the injection process. The retraction mechanism may be designed to retract the needles back into the detachable needle cartridge 206 after the complete injection of the medicine. The retraction of the needles may be facilitated by a spring mechanism, which may be coupled to the needles. Upon completion of the injection process, the spring mechanism may be activated, causing the needles to retract back into the detachable needle cartridge 206. This feature may serve to prevent tissue damage and minimize pain and discomfort for the subject.

The spring mechanism may be designed to return to its original position after the retraction of the needles, readying the device for subsequent use. In another embodiment of the present disclosure, the spring mechanism may also be designed to provide tactile or audible feedback after the retraction of the needles, providing an additional layer of subject assurance. The feedback may be generated by the movement of the spring and needles, or it may be generated by a separate feedback mechanism integrated into the medical device 100.

In some aspect, the retraction mechanism may be integrated into the detachable needle cartridge as a single unit for simplicity. In another aspect, the retraction mechanism may be a separate component that can be attached to the detachable needle cartridge, allowing for easier replacement or maintenance of the mechanism. Regardless of the specific design, the retraction mechanism may be designed to work in conjunction with the release injectable button and the spring-loaded plunger mechanism to provide a reliable and efficient injection process.

In another embodiment of the present disclosure, the retraction mechanism may be designed to accommodate a variety of needle sizes and types. For instance, the retraction mechanism may be designed to accommodate needles of different lengths, diameters, or shapes, providing flexibility in the design and operation of the medical device 100. The retraction mechanism may also be designed to accommodate a variety of needle materials, including but not limited to stainless steel, nickel-plated steel, or alloy coated aluminum needles. These materials may offer sharpness and durability, ensuring efficient delivery of the medicine into the subject body.

In another aspect of the present disclosure, the retraction mechanism may be designed to retract the needles at a specific speed or rate. The speed or rate may be controlled to prevent tissue damage and minimize pain and discomfort for the subject. The speed or rate of retraction may be adjusted based on factors such as the thickness of the subject skin, the desired depth of injection, and the specific treatment procedure. For instance, a slower rate of retraction may be used for superficial injections, while a faster rate of retraction may be used for deeper injections. Regardless of the specific speed or rate of retraction, the retraction mechanism may be designed to provide a comfortable and efficient injection experience for the subject.

Figure 7:
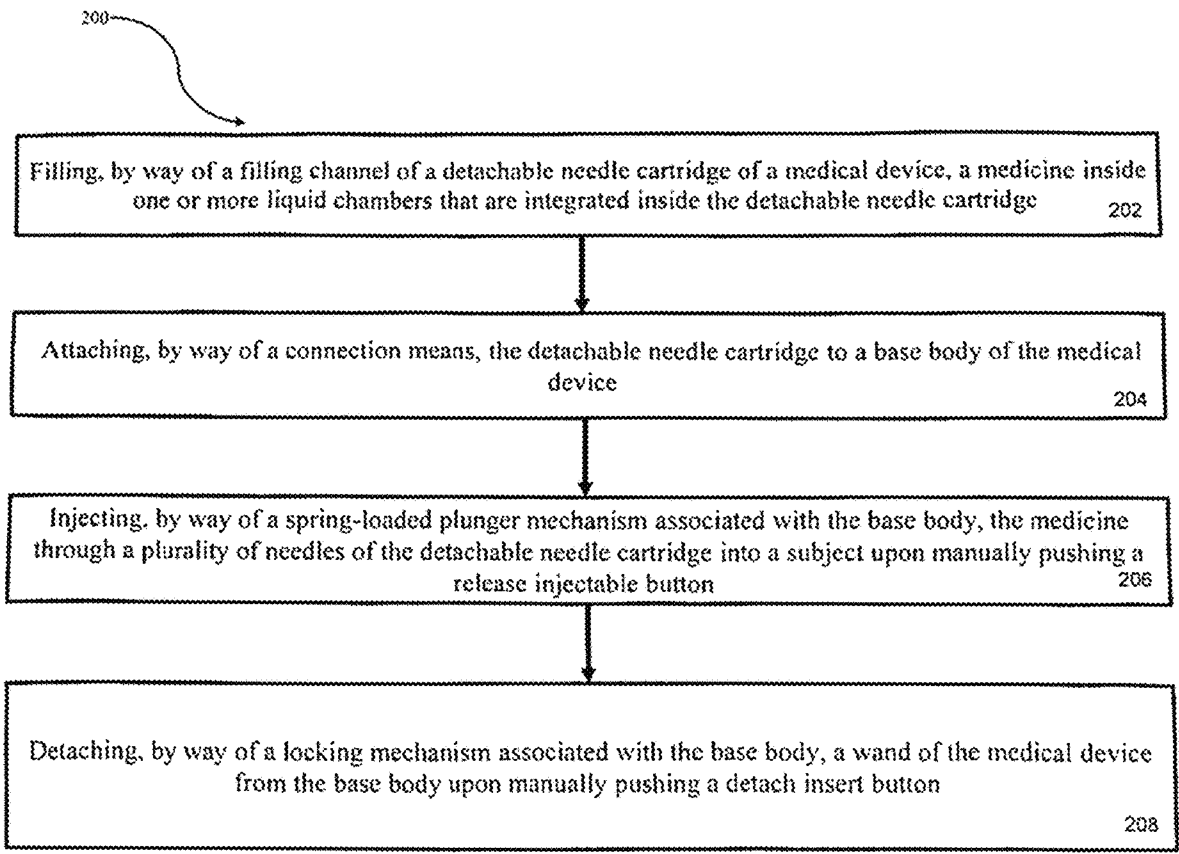
FIG. 7 illustrates flowchart of a method for injecting through the medical device, according to an embodiment of the present disclosure.

FIG. 7 illustrates the method of injecting medicine through the medical device, according to an embodiment of the present disclosure. The medical device 100 may include a method 200 for injecting medicine. The method may involve several steps, including filling, attaching, injecting, and detaching.

In the filling step 202, a drug or medicine may be filled inside one or more liquid chambers 105 of the detachable needle cartridge 106. This filling may be facilitated by the filling channel 107 disposed on the outer surface of the detachable needle cartridge 106. The filling channel 107 may be designed to allow for easy and efficient filling of the liquid, reducing the time and effort required for the filling process. In another embodiment, the filling channel 107 may include a tamper-evident seal 115, and a closure cap 117 disposed on the tamper-evident seal to prevent the entry of moisture and oxygen into the liquid chamber 105, ensuring the integrity and sterility of the liquid.

In the attaching step 204, the detachable needle cartridge 106 may be coupled to the base body 102. This coupling may be facilitated by a connection means (103*a*, 103*b*, 103*c*), which may be selected from a group of sliding fit, snap-fit, push-fit, bayonet fitting, threaded-fitting, and the like. This allows for easy attachment and detachment of the detachable needle cartridge 106, facilitating replacement or cleaning of the detachable needle cartridge 106.

In the injecting step 206, the liquid inside the liquid chamber 105 may be expelled out to the plurality of needles 114 of the detachable needle cartridge 106. This expulsion may be facilitated by the spring-loaded plunger mechanism coupled to the release injectable button 108. Upon pushing the release injectable button 108, the spring-loaded plunger mechanism may be activated, causing the liquid to be injected into the plurality of needles 114 of the detachable needle cartridge 106. The spring-loaded plunger mechanism may be designed to return to its original position after injecting the liquid into the subject, readying the medical device 100 for subsequent use.

In the detaching step 208, the wand 104 coupled to the base body 102 may facilitate the detachment of the wand 104 from the base body 102. This detachment may be facilitated by the detach insert button 109 that unlocks the locking mechanism 111 of the wand 104 inside the base body 102. Upon pushing the detach insert button 109, the wand 104 may be detached from the base body 102, allowing for sterilizing or autoclaving of the base body 102 after the injecting process.

In another embodiment, the method 200 for injecting medicine may provide tactile or audible feedback after the complete injection of the medicine or liquid. The feedback may serve to indicate to the subject that the injection process has been successfully completed, enhancing the subject experience and ensuring proper operation of the medical device 100.

In another aspect, the method 200 for injecting medicine may be designed to accommodate a variety of medicines, drugs, antibiotics, pharmaceutical compositions, cosmetic liquids or gels and the like, providing a versatile solution for various medical applications. The specific type of medicine used may depend on the specific treatment or medical procedure being performed. For instance, in some aspect, the medicine may be a drug designed to treat a specific disease or condition. In another aspect, the medicine may be an antibiotic designed to fight a specific infection. Regardless of the specific type of medicine used, the injection or the device may be used to administer drugs and substances for cosmetic enhancements, such as hair regrowth, reducing wrinkles, skin plumping, and reducing or eliminating sweating.

In another embodiment, the detachable needle cartridge 106 may include additional features to enhance its functionality and subject experience. For instance, the detachable needle cartridge 106 may include a closure cap 117 and a tamper-evident seal 115. The closure cap 117 may be designed to securely seal the filling channel 107 after the liquid has been filled into the liquid chamber 105, preventing leakage or spillage of the liquid. The tamper-evident seal 115 may be designed to provide visible evidence if the filling channel 107 has been tampered with or opened after the liquid has been filled. This feature may serve to ensure the integrity and sterility of the liquid in the liquid chamber 105, preventing contamination by moisture, oxygen, or other contaminants.

In another embodiment of the present disclosure, the detachable needle cartridge 106 may include a sensor (not shown) selected from the group of a pressure sensor, a flow rate sensor, or an optical sensor, coupled with the one-way valve 116. This sensor may be designed to detect liquid depletion in the liquid chamber 105, providing an additional layer of assurance to the subject. The sensor may be sensitive enough to accurately detect the end of liquid, ensuring that the entire volume of liquid is delivered to the subject. The sensor may be integrated into the detachable needle cartridge 106 as a single unit for simplicity, or it may be a separate component that can be attached to the detachable needle cartridge 106, allowing for easier replacement or maintenance of the sensor.

In another embodiment of the present disclosure, the detachable needle cartridge 106 may include a needle shield 113. The needle shield 113 may be coupled with the plurality of needles 114 within the detachable needle cartridge 106. The needle shield 113 may serve to protect the plurality of needles 114 when the medical device 100 is not in use, preventing accidental needle sticks and maintaining the sterility of the plurality of needles 114. The needle shield 113 may be made of a durable material, such as plastic or metal, to provide effective protection for the needles. In some aspect, the needle shield 113 may be designed to be easily removed or retracted when the medical device 100 is ready for use. In another aspect, the needle shield 113 may be integrated into the detachable needle cartridge 106 and may automatically retract or move aside during the injection process. Regardless of the specific design, the needle shield 113 may enhance the safety and usability of the medical device 100.

In another embodiment of the present disclosure, the detachable needle cartridge 106 may include an indicator or marking 119. The indicator or marking 119 may be designed to ensure proper fitting of the detachable needle cartridge 106 in the base body 102 of the medical device 100. The indicator or marking 119 may be located on the outer surface of the detachable needle cartridge 106 and may be visible to the subject during the attachment process. The indicator or marking 119 may be of any suitable shape, size, color, or design that allows for easy recognition by the subject. For instance, the indicator or marking 119 may be a line, dot, arrow, or any other suitable symbol. In some aspect, the indicator or marking 119 may be colored to enhance visibility. The indicator or marking 119 may be designed to align with a corresponding indicator or marking on the base body 102 when the detachable needle cartridge 106 is properly fitted. This feature may provide a visual confirmation to the subject that the detachable needle cartridge 106 has been correctly attached, enhancing the subject experience and ensuring proper operation of the medical device 100. In another aspect, the detachable needle cartridge 106 may not include an indicator or marking 119, and the proper fitting of the detachable needle cartridge 106 in the base body 102 may be determined by other means, such as tactile feedback or the coupling mechanism.

In another embodiment of the present disclosure, the medical device 100 may be used by medical practitioner or veterinarians for medical procedures such as cosmetic procedures like Botox treatment and non-cosmetic procedures like hyperhidrosis treatment that require multiple times of medicine injection into the subject. The medical device 100 may allow for a large area to be injected in several spots at a single time.

Although preferred embodiments have been depicted and described in detail herein, it will be apparent to those skilled in the relevant art that various modifications, additions, substitutions and the like can be made without departing from the spirit of the disclosure, and these are, therefore, considered to be within the scope of the disclosure, as defined in the following claims. Features or functionality described with respect to certain example embodiments may be combined and sub-combined in and/or with various other example embodiments. Also, different embodiments and/or elements of example embodiments, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, can be at least partially performed via at least one entity or actor in any manner.

The terminology used herein can imply direct or indirect, full or partial, temporary or permanent, action or inaction. For example, when an element is referred to as being “on,” “connected” or “coupled” to another element, then the element can be directly on, connected or coupled to the other element and/or intervening elements can be present, including indirect and/or direct variants. In contrast, when an element is referred to as being “directly connected” or “directly coupled” to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from the teachings of the present disclosure.

The terminology used herein is for describing particular example embodiments and is not intended to be necessarily limiting of the present disclosure. As used herein, the singular forms “a,” “an” and “the” are intended to include the plural forms as well, unless the context clearly indicates otherwise. The terms “comprises,” “includes” and/or “comprising," "including" when used in this specification, specify the presence of stated features, integers, steps, operations, elements, and/or components, but do not preclude the presence and/or addition of one or more other features, integers, steps, operations, elements, components, and/or groups thereof.

As used herein, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

As used herein, the term "about" and/or "substantially" refers to a +/−10% variation from the nominal value/term. Such variation is always included in any given.

If any disclosures are incorporated herein by reference and such disclosures conflict in part and/or in whole with the present disclosure, then to the extent of conflict, and/or broader disclosure, and/or broader definition of terms, the present disclosure controls. If such disclosures conflict in part and/or in whole with one another, then to the extent of conflict, the later-dated disclosure controls.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Whereas many alterations and modifications of the present invention will no doubt become apparent to a person of ordinary skill in the art after having read the foregoing description, it is to be understood that the particular embodiments shown and described by way of illustration are in no way intended to be considered limiting.

The invention claimed is:

1. A method for injecting medicine through a medical device, the method comprising:

filling, by way of a filling channel of a detachable needle cartridge of a medical device, the medicine inside one or more liquid chambers that are integrated inside the detachable needle cartridge;

attaching, by way of a connection means, the detachable needle cartridge to a base body of the medical device;

injecting, by way of a spring-loaded plunger mechanism associated with the base body, the medicine through a plurality of needles of the detachable needle cartridge into a subject upon manually pushing a release injectable button; and detaching, by way of a locking mechanism associated with the base body, a wand of the medical device from the base body upon manually pushing a detach insert button.

2. The method of claim 1, wherein the filling channel of the detachable needle cartridge further comprising a tamper-evident seal, and a closure cap disposed on the tamper-evident seal.

3. The method of claim 1, wherein the filling channel has a plastic material selected from a group of polypropylene, polycarbonate, polyethylene, polystyrene, or silicone.

4. A medical device, comprising:

a base body, comprising:
a release injectable button;
a spring-loaded plunger mechanism;

a detachable needle cartridge coupled to the base body and comprising:
one or more liquid chambers integrated inside the detachable needle cartridge and configured to hold liquid;
a filling channel disposed on an outer surface of the detachable needle cartridge and facilitates filing of liquid in the one or more liquid chambers;
a plurality of needles coupled to the one or more liquid chambers; and a wand coupled to the base body and comprising:
a detach insert button;

wherein the base body is adapted to activate the spring-loaded plunger mechanism by manually pushing the release injectable button and releases the liquid into the plurality of needles of the detachable needle cartridge to be injected into a subject; and wherein the wand adapted to attach and detach from the base body by way of a locking mechanism activated by manually pushing the detach insert button.

5. The medical device of claim 4, wherein the spring-loaded plunger mechanism comprising a spring adapted to maintain an expanded state before injecting the liquid into the detachable needle cartridge and attains a compressed state upon activation of the release injectable button to inject the liquid into the detachable needle cartridge.

6. The medical device of claim 4, wherein the wand further comprising the locking mechanism selected from a group of looking teeth, latch bolt, locking pin, or bayonet fitting.

7. The medical device of claim 4, wherein the base body is at least one of a paddle-shape.

8. The medical device of claim 4, wherein the release injectable button and detach insert button further comprising a tactile or audible feedback to indicate the pushing of each button.

9. The medical device of claim 4, wherein the base body comprises of metal has a material selected from a group of stainless steel, titanium, or coated aluminum.

10. The medical device of claim 4, wherein the detachable needle cartridge has a disposable and heat-resistant material selected from a group of polypropylene, polycarbonate, polyethylene, polystyrene, or silicone.

11. The medical device of claim 4, wherein the liquid is at least one of a medicine, drug, antibiotics, pharmaceutical compositions, cosmetic liquids or gels.

12. The medical device of claim 4, wherein the detachable needle cartridge further comprising a connection means selected from a group of sliding fits, snap-fit, push-fit, bayonet fitting, threaded-fitting and the like.

13. The medical device of claim 4, wherein the one or more liquid chambers have a volume in the range between 1.5 to 8 cubic centimeters.

14. The medical device of claim 4, wherein the plurality of needles have a material selected from a group of stainless steel, nickel-plated steel, or alloy coated aluminum needles.

15. The medical device of claim 4, wherein the plurality of needles of the detachable needle cartridge inclined at an acute angle to facilitate insertion of the needles into the subject with ease.

16. A detachable needle cartridge medical device, comprising:

a base body;

a detachable needle cartridge comprising:

one or more liquid chambers integrated inside the detachable needle cartridge and configured to hold liquid;

a filling channel disposed on an outer surface of the detachable needle cartridge and facilitates filling of liquid in the one or more liquid chambers, wherein the filling channel of the detachable needle cartridge further comprises a tamper-evident seal, and a closure cap disposed on the tamper-evident seal;

a plurality of needles or multiple spring-loaded autoinjectors coupled to the one or more liquid chambers;

a one-way valve integrated with the plurality of needles or the multiple spring-loaded autoinjectors; and a connection means;

a wand coupled to the base body and comprising a detach insert button;

wherein the detachable needle cartridge is coupled to the base body by way of the connection means and is adapted to deliver the liquid through the plurality of needles or the multiple spring-loaded autoinjectors injected into a subject; and wherein the wand is adapted to attach to and detach from the base body by way of a locking mechanism activated by manually pushing the detach insert button, the locking mechanism comprising at least one of locking teeth configured to engage one or more corresponding grooves or notches on the base body, a latch bolt, a locking pin, or a bayonet fitting.

17. The needle cartridge of claim 16, wherein the multiple spring-loaded autoinjectors is retracted back after the complete injection of the medicine from the one or more liquid chambers to prevent tissue damage and minimize pain discomfort.

18. The needle cartridge of claim 16, wherein the detachable needle cartridge further comprising the connection means selected from a group of sliding fit, snap-fit, push-fit, bayonet fitting, or threaded-fitting.

19. The needle cartridge of claim 16, wherein the plurality of needles is at least 20, 30, or 40 needles depending on a treatment procedure.

20. The needle cartridge of claim 16, further comprising one or more needle shield coupled with the plurality of needles of the detachable needle cartridge.

21. The needle cartridge of claim 16, wherein the plurality of needles of the detachable needle cartridge inclined at an acute angle to facilitate easy insertion of the plurality of needles into the subject.

22. The needle cartridge of claim 16, further comprising at least one indicator or marking on the detachable needle cartridge that ensures proper fitting of the detachable needle cartridge in the base body.

23. The needle cartridge of claim 16, wherein the plurality of needles has a material selected from a group of stainless steel, nickel-plated steel, or alloy coated aluminum needles.

24. The needle cartridge of claim 16, wherein the needle cartridge has a disposable and heat-resistant material selected from a group of polypropylene, polycarbonate, polyethylene, polystyrene, or silicone.

* * * * *